US010912731B2

(12) United States Patent
Myers et al.

(10) Patent No.: US 10,912,731 B2
(45) Date of Patent: Feb. 9, 2021

(54) BIPHASIC ORAL CARE COMPOSITIONS

(71) Applicant: Colgate-Palmolive Company, New York, NY (US)

(72) Inventors: Carl Myers, Wayne, NJ (US); Rehana Begum-Gafur, Clifton, NJ (US); Jeffrey Merl Miller, Jackson, NJ (US); Ekta Makwana, Monroe, NJ (US)

(73) Assignee: Colgate-Palmolive Company, New York, NY (US)

( * ) Notice: Subject to any disclaimer, the term of this patent is extended or adjusted under 35 U.S.C. 154(b) by 50 days.

(21) Appl. No.: 15/668,913

(22) Filed: Aug. 4, 2017

(65) Prior Publication Data

US 2019/0038545 A1 Feb. 7, 2019

(51) Int. Cl.
| *A61K 8/86* | (2006.01) |
| *A61Q 11/00* | (2006.01) |
| *A61K 8/84* | (2006.01) |
| *A61K 8/24* | (2006.01) |
| *A61K 8/44* | (2006.01) |
| *A61K 8/03* | (2006.01) |
| *A61Q 17/00* | (2006.01) |

(52) U.S. Cl.
CPC .................. *A61K 8/86* (2013.01); *A61K 8/03* (2013.01); *A61K 8/24* (2013.01); *A61K 8/44* (2013.01); *A61K 8/84* (2013.01); *A61Q 11/00* (2013.01); *A61K 2800/30* (2013.01); *A61K 2800/48* (2013.01); *A61Q 17/005* (2013.01)

(58) Field of Classification Search
None
See application file for complete search history.

(56) References Cited

U.S. PATENT DOCUMENTS

| 3,864,472 | A | * | 2/1975 | Pensak | A61K 8/416 |
| | | | | | 424/54 |
| 5,723,106 | A | * | 3/1998 | Buch | A61K 8/34 |
| | | | | | 424/49 |
| 6,521,216 | B1 | * | 2/2003 | Glandorf | A61K 8/02 |
| | | | | | 424/49 |
| 8,926,997 | B1 | | 1/2015 | Stockel et al. | |
| 9,408,794 | B2 | | 8/2016 | Lewus et al. | |
| 9,579,269 | B2 | | 2/2017 | Mello et al. | |
| 9,801,795 | B2 | | 10/2017 | Nesta et al. | |
| 9,968,528 | B2 | | 5/2018 | Xu et al. | |
| 2011/0052509 | A1 | * | 3/2011 | Subramanyam | A61K 8/19 |
| | | | | | 424/52 |
| 2016/0331670 | A1 | | 11/2016 | Prencipe et al. | |
| 2017/0128340 | A1 | | 5/2017 | Mello et al. | |
| 2017/0151158 | A1 | | 6/2017 | Myers et al. | |
| 2018/0228704 | A1 | | 8/2018 | Xu et al. | |

FOREIGN PATENT DOCUMENTS

| WO | WO-92010994 | * | 7/1992 | ............... A61K 7/16 |
| WO | WO-98043603 | * | 3/1998 | ............... A61K 7/16 |
| WO | 2008/058820 | | 5/2008 | |
| WO | 2011/162756 | | 12/2011 | |
| WO | WO 2012/064338 | | 5/2012 | |
| WO | 2014/094225 | | 6/2014 | |
| WO | 2015/094333 | | 6/2015 | |
| WO | WO 2015/094336 | | 6/2015 | |
| WO | WO-2015094336 A1 | * | 6/2015 | ............. C08L 43/02 |
| WO | 2017/096000 | | 6/2017 | |

OTHER PUBLICATIONS

International Search Report and Written Opinion of the International Searching Authority in International Application No. PCT/US2017/045436, dated Jun. 20, 2018.
International Search Report of International Application No. PCT/US2016/064349, dated Feb. 27, 2017, 4 pages.

* cited by examiner

*Primary Examiner* — Celeste A Roney

(57) ABSTRACT

This application provides, among other things, novel aqueous biphasic oral care compositions comprising two distinct aqueous phases, useful for combining and delivering poorly compatible ingredients, for example to deliver effective levels of cationic antibacterial agents in combination with anionic polymers, e.g. that protect against erosion and staining, by addition of a stabilizing amount of a polyamine, e.g. lysine, and methods for making and using the same.

15 Claims, No Drawings

BIPHASIC ORAL CARE COMPOSITIONS

BACKGROUND

This application relates, inter alia, to novel aqueous biphasic oral care compositions useful for combining and delivering poorly compatible ingredients, for example to deliver effective levels of cationic antibacterial agents in combination with polymers that protect against erosion and staining.

Biofilms form when bacteria adhere to surfaces in some form of watery environment and begin to excrete a slimy, glue-like substance that can stick to all kinds of materials—metals, plastics, soil particles, medical implant materials, biological tissues. Dental plaque is a biofilm that adheres to tooth and other oral surfaces, particularly at the gingival margin, and is implicated in the occurrence of gingivitis, periodontitis, caries and other forms of periodontal disease. Dental plaque is cohesive and highly resistant to removal from teeth and/or oral surfaces. Bacteria associated with dental plaque convert sugar to glucans, which are insoluble polysaccharides that provide plaque with its cohesive properties. Anaerobic bacteria in plaque metabolize sugar to produce acids that dissolve tooth minerals, damaging the enamel and eventually forming dental caries. Saliva can buffer acids produced by bacteria and promote remineralization of the enamel, but extensive plaque can block the saliva from contact with the enamel. Redeposition of minerals in the biofilm forms a hard deposit on the tooth called calculus (or tartar), which becomes a local irritant for the gums, causing gingivitis.

Various antibacterial agents can retard the growth of bacteria and thus reduce the formation of biofilm on oral surfaces. In many cases, these antibacterial agents are cationic, for example quaternary ammonium surfactants such as cetyl pyridinium chloride (CPC), bisguanides such as chlorhexidine, metal cations such as zinc or stannous ions, and guanidines such as arginine.

Everyday activities such as smoking or other oral use of tobacco products, and eating, chewing or drinking certain foods and beverages (particularly coffee, tea, cola drinks, and red wine), cause undesirable staining of surfaces of teeth. Staining can also result from microbial activity, including that associated with dental plaque. The chromogens or color causing substances in these materials become part of the pellicle layer and can permeate the enamel layer. Even with regular brushing and flossing, years of chromogen accumulation can impart noticeable tooth discoloration.

A tooth is comprised of an inner dentin layer and an outer hard enamel layer that is the protective layer of the tooth. The enamel layer of a tooth is naturally opaque, and white or a slightly off-white color. The enamel layer is composed of hydroxyapatite mineral crystals that create a somewhat porous surface. These hydroxyapatite crystals form microscopic hexagonal rods or prisms that make up the enamel surface. As a result, the surface of the enamel presents microscopic spaces or pores between the prisms. Without limiting the mechanism, function, or utility of the present disclosure, it is believed that this porous nature of the enamel is where discoloring substances permeate the enamel and discolor the teeth.

As the compounds that stain the teeth are typically anionic materials, cationic antibacterial agents can cause or enhance staining by facilitating the deposit of chromogens or by forming salts with minerals.

Anionic polymers have been shown to reduce staining and erosion as well as reduce biofilm formation can help coat and protect the enamel, discouraging bacterial attachment and repelling chromogens. These polymers, however, can interact with cationic antimicrobial agents, leading to formulation incompatibilities, particularly in high water formulations, such as mouthwashes, and inhibiting delivery of the antimicrobial agent and/or the polymer. Oral care products comprising such polymers are disclosed, for example, in WO 2015094336 A1, incorporated herein by reference.

One approach to maintaining separation of anionic polymers and cationic antimicrobial agents is through the use of a biphasic system that separates these components into distinct liquid phases. Typically, such compositions are shaken just prior to use so that both phases are mixed. After use, the composition is left to stand and separate into distinct phases-normally a hydrophilic phase and a hydrophobic phase. However, many common components used in oral care compositions have both hydrophilic and hydrophobic characteristics, which creates a barrier to efficient phase separation. For example, many commonly used orally-acceptable polymers contain both hydrophilic copolymer blocks and hydrophobic copolymer blocks, which may hinder or prevent separation of phases. These ingredients may lead to long separation times or may prevent the composition from separating into phases entirely.

There is thus a need for novel biphasic compositions and methods that minimize interactions between incompatible ingredients in a formulation, enhance separation of hydrophobic and hydrophilic phases, and inhibit staining and/or biofilm formation.

BRIEF SUMMARY

It is surprisingly found that formulations comprising an aqueous solution of an acidic polymer, e.g., having an isoelectric point of less than pH 5; a nonionic polymer, e.g. a poly(alkylene oxide); at least one polyphosphate; a polyamine compound, e.g., having an isoelectric point of at least pH 8.5, e.g., pH 9-10, e.g., lysine in free or salt form; and water, can form an unusual biphasic system, wherein the polyamine compound interacts with the acidic polymer to form one aqueous phase while the nonionic polymer separates to form a second aqueous phase, the two phases thus both being aqueous, yet having different compositions and densities.

If the formulations are shaken to mix the phases, the phases will re-separate when the material is at rest. In certain embodiments, a cationic agent, for example a cationic antibacterial agent, may be included in the formulation, which will be concentrated in the lower phase. The biphasic character provides interesting aesthetic effects, as the addition of a dye makes the two phases visually distinct, and the formulation moreover provides functional benefits by enabling the combination of agents that would otherwise be incompatible. When the phases are mixed, for example by shaking before use, the anionic polymer and any cationic agent are delivered in microdroplets having a relatively high concentration of the anionic polymer and, where present, the cationic active, thus providing improved delivery and a high local concentration of the active at the site of delivery, compared to a homogenous solution. These formulations differ from conventional biphasic formulations in that both phases are aqueous, rather than one phase being hydrophobic and the other hydrophilic. They also differ from structured compositions such as gels insofar as they separate into phases having different densities, e.g., an upper phase and a lower phase, which can be readily mixed by shaking, and which will then re-separate at rest within a short period.

The degree of separation, the relative proportions of the two layers, and the time needed to form two discrete layers can be tuned by varying the polymer, polyphosphate and polyamine levels. The dual phase, with a distinct top and bottom layer, each containing different materials and potentially different actives, or at least different concentrations of active, is useful in a variety of applications, e.g., for oral care, for example in a mouth wash or other rinse product.

It has surprisingly been found that phosphate anions show substantial ability to induce phase partitioning than other functional groups having the same charge. The phosphate salts used herein (e.g., sodium tripolyphosphate, sodium acid pyrophosphate) have a significantly higher affinity for the bottom phase, i.e., hydrophilic phase, which reduces the time necessary for phase separation. By replacing ingredients having both hydrophilic and hydrophobic properties, such as co-polymers of methyl vinyl ether and maleic anhydride (i.e., Gantrez S-97), with polyphosphates as disclosed herein has been found to decrease separation time, decrease viscosity to levels more suitable for a mouthwash composition, and maintain separability at a wider range of pH.

In certain embodiments, the invention provides compositions that form a biphasic aqueous solution using only water soluble materials and no oil. In other embodiments, the aqueous biphasic composition is further combined with an oil phase to give a three-phase system, wherein two of the phases are aqueous and the third is oil-based. In one example, the top layer is composed primarily of mineral oil, the middle layer primarily of water and nonionic polymer, and the bottom layer primarily of anionic polymer and polyamine. These three phases will mix when agitated, and then the layers will separate at rest. This allows for the delivery of further combinations of otherwise insoluble or incompatible active compounds.

For example, cetyl pyridinium chloride (CPC) is useful as an antibacterial agent, while anionic polymers may be useful to help remove and inhibit staining. These ingredients are generally incompatible because they interact, resulting in reduced efficacy both ingredients or even precipitation of both components. The addition of lysine provides needed stability and competition between the acid functional groups of the polymer, the acid and the amine functional groups of lysine, and the CPC—the result is to free CPC and make it more available for interaction with bacteria. In some embodiments, the addition of glutamic acid further improves CPC availability through additional competition pathways through the carboxylates on glutamic acid. Without lysine (and optionally glutamic acid), a formulation with CPC and anionic polymers may have little better efficacy than a non-CPC containing material, or the media control.

Similarly, chlorhexidine will generally complex with anionic polymers no matter what steps are taken, given their high charge density and entropically driven precipitation reaction. But we have found that chlorhexidine and anionic polymers can be formulated in such a way to prevent precipitation (or to re-dissolve the precipitate) through the inclusion of one or more polyphosphates, lysine (Lys), and polyethylene glycol (PEG). Additionally, a non-ionic surfactant, e.g., poloxamer, can be used to supplement the composition.

The disclosure thus provides, in one embodiment, compositions comprising an aqueous solution of
(i) an acidic polymer, for example a polymer having an isoelectric point of less than pH 5, e.g., a phosphate/acrylate co-polymer, for example a polymer made up of acrylate monomers and phosphate-bearing monomers, e.g., a co-polymerized product of a mixture of acrylic acid, methacrylic acid, and a mixture of compounds of Formula 1:

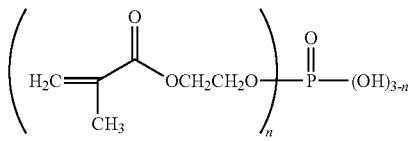

wherein n is 0, 1 or 2; and mixtures thereof; e.g., wherein the orally acceptable acidic polymer has a molecular weight of at least 7500D, e.g., 10 kD to 1500 kD;
(ii) a nonionic polymer, for example selected from one or more poly(alkylene oxide) polymers, e.g., selected from polyethylene glycols, polypropylene glycols, poloxamers and mixtures thereof; e.g., wherein the nonionic polymer has a molecular weight of at least 3000D, e.g., 6 kD to 250 kD, e.g., 8 kD;
(iii) at least one polyphosphate present in an amount to facilitate separation of the two distinct aqueous phases, wherein the polyphosphate comprises sodium tripolyphosphate, tetrasodium pyrophosphate, sodium acid pyrophosphate, tetrapotassium pyrophosphate, sodium hexametaphosphate or combinations thereof;
(iv) a stabilizing amount of a polyamine, e.g., having an isoelectric point of greater than pH 8.5, e.g., lysine, e.g., which may be added in free or salt form;
(v) an orally acceptable carrier; and
(v) water;
wherein the solution comprises two distinct aqueous phases having different composition and density.

The disclosure further provides methods of using such compositions, for example, inhibiting dental erosion, staining, and/or biofilm formation.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

As is usual in the art, the compositions described herein are sometimes described in terms of their ingredients, notwithstanding that the ingredients may disassociate, associate or react in the formulation. Ions, for example, are commonly provided to a formulation in the form of a salt, which may dissolve and disassociate in aqueous solution. It is understood that the invention encompasses both the mixture of described ingredients and the product thus obtained.

In a first embodiment, the disclosure provides an oral care composition (Composition 1) comprising an aqueous solution of
an acidic polymer;
a nonionic polymer;
at least one polyphosphate;
a stabilizing amount of a polyamine compound;
an orally acceptable carrier; and
water;
wherein the solution comprises two distinct aqueous phases having different composition and density.

For example, the disclosure provides embodiments of Composition 1 as follows:

1.1 Composition 1, wherein the polyphosphate is present in an amount to facilitate separation of the two distinct aqueous phases.
1.2 Composition 1 or 1.1, wherein the polyphosphate comprises sodium tripolyphosphate, tetrasodium pyrophosphate, sodium acid pyrophosphate, tetrapotassium pyrophosphate, sodium hexametaphosphate or combinations thereof.
1.3 Any foregoing composition, wherein the polyphosphate comprises a combination of sodium tripolyphosphate and sodium acid pyrophosphate.
1.4 Any foregoing composition, wherein the polyphosphate consists of a combination of sodium tripolyphosphate and sodium acid pyrophosphate.
1.5 Any foregoing composition, wherein the at least one polyphosphate is present in an amount of about 0.1-7 weight % based on the total weight of the composition, 1-6 weight % based on the total weight of the composition, 2-5 weight % based on the total weight of the composition, 3-5 weight % based on the total weight of the composition, or 4-5 weight % based on the total weight of the composition.
1.6 Any foregoing composition, wherein the at least on polyphosphate comprises sodium tripolyphosphate in an amount of 0.1-4 weight % and sodium acid pyrophosphate in an amount of 0.1-4 weight % based on the total weight of the composition; or sodium tripolyphosphate in an amount of 2-3 weight % and sodium acid pyrophosphate in an amount of 2-3 weight % based on the total weight of the composition.
1.7 Any foregoing composition wherein the acid polymer is in linear or branched form or mixtures thereof, having acidic functional groups to provide an isoelectric point of pH 5 or less, and optionally additionally having uncharged spacers or side chains, for example comprising hydrophobic moieties (such as methyl methacrylate monomers or alkane chains), and/or uncharged hydrophilic moieties (such as polyalkylene glycols).
1.8 Any foregoing composition wherein the acidic polymer is selected from one or more of synthetic anionic linear or branched polycarboxylates, phosphate/acrylate co-polymers, linear or branched sulfates and combinations thereof.
1.9 Any foregoing composition wherein the acidic polymer is selected from one or more of co-polymerized products of a mixture of acrylic acid, methacrylic acid, and a mixture of compounds of Formula 1:

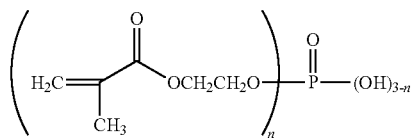

wherein n is 0, 1 or 2; and mixtures thereof;
e.g., wherein the orally acceptable acidic polymer has a molecular weight of at least 7500D, e.g., 10 kD to 1500 kD.

1.10 Any foregoing composition wherein the acidic polymer comprises a phosphate/acrylate co-polymer which is a co-polymerized product of a mixture of acrylic acid, methacrylic acid, and a mixture of compounds of Formula 1:

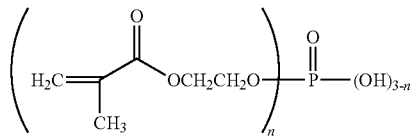

wherein n is 0, 1 or 2.

1.11 Any foregoing composition wherein the acidic polymer comprises a phosphate/acrylate co-polymer, wherein the phosphate/acrylate co-polymer is a co-polymerized product of a mixture of acrylic acid, methacrylic acid, and 2-hydroxyethyl methacrylate phosphates of Formula 1 comprising acrylic acid in a molar percentage of 80-90%, e.g., about 85%; methacrylic acid in a molar percentage of 5-15%, e.g., about 11%, and hydroxyethyl methacrylate phosphates of Formula 1 in a molar percentage of 2-6%, e.g., about 4%.
1.12 Any foregoing composition wherein the acidic polymer comprises a phosphate/acrylate co-polymer, wherein the phosphate/acrylate co-polymer has an average molecular weight of from 10 to 40 kDa, e.g., 20 to 30 kDa.
1.13 Any foregoing composition wherein the acidic polymer comprises a phosphate/acrylate co-polymer, wherein the phosphate/acrylate copolymer is a random copolymer having a weight average molecular weight of about 20,000 to 30,000 grams per mole that is the copolymerized product of a mixture of acrylic acid, methacrylic acid, and 2-hydroxyethy methacrylate phosphates of Formula 1, e.g., in a molar ratio of about 85:11:4.
1.14 Any foregoing composition wherein the acidic polymer comprises 0.1 to 10 weight % phosphate/acrylate co-polymer, e.g., 0.2 to 9 weight % phosphate/acrylate co-polymer, e.g., 0.3 to 8 weight % phosphate/acrylate co-polymer, e.g., 0.4 to 7 weight % phosphate/acrylate co-polymer, e.g., 0.5 to 6 phosphate/acrylate co-polymer, e.g., e.g., 0.5 to 5 weight % phosphate/acrylate co-polymer, e.g., 0.5 to 4 weight % phosphate/acrylate co-polymer, e.g., 0.5 to 3 weight % phosphate/acrylate co-polymer, e.g., 0.5 to 2 weight % phosphate/acrylate co-polymer, e.g., 1 to 10 weight %/O phosphate/acrylate co-polymer, e.g., 1 to 8 weight %/o phosphate/acrylate co-polymer, e.g., 1 to 6 weight % phosphate/acrylate co-polymer, e.g., 1 to 5 weight %/o phosphate/acrylate co-polymer, e.g., 1 to 4 weight % phosphate/ acrylate co-polymer, e.g., 1 to 3 weight % phosphate/acrylate co-polymer, e.g., 1 to 2 weight % phosphate/acrylate co-polymer.

1.15 Any foregoing composition wherein the acidic polymer is present in a total amount of 0.1-5 weight % based on the total weight of the composition; or 2-4 weight % based on the total weight of the composition.

1.16 Any foregoing composition wherein the acidic polymer comprises a phosphate/acrylate co-polymer, in an amount of 1 to 12%; e.g., 2-4%.

1.17 Any foregoing composition wherein the nonionic polymer is selected from one or more poly(alkylene oxide) polymers.

1.18 Any foregoing composition wherein the nonionic polymer is selected from polyethylene glycols, polypropylene glycols, poloxamers, co-polymers of polyethylene glycol and polypropylene glycol, and mixtures thereof.

1.19 Any foregoing composition wherein the nonionic polymer has a molecular weight of at least 3000D, e.g., 6 kD to 250 kD, e.g., 8 kD.

1.20 Any foregoing compositions wherein the nonionic polymer comprises polyethylene glycol of MW 5 kDa-35 kDa, in an amount of 3% to 8% by weight; e.g. 4% to 6% by weight; e.g., 4%; e.g., 5/0%.

1.21 Any foregoing compositions wherein the nonionic polymer is 3-6% polyethylene glycol having a molecular weight of 5 kDa to 10 kDa, e.g. 8 kDa.

1.22 Any foregoing composition wherein the polyamine compound comprises lysine, in free or salt form.

1.23 Any foregoing composition wherein the stabilizing amount of polyamine compound, is an amount sufficient to substantially interfere with interaction between the at least one polyphosphate and/or an optional a cationic active agent and the acidic polymer, e.g. an amount sufficient to inhibit formation of a precipitate or reduction of the efficacy of the cationic active agent.

1.24 Any foregoing composition wherein the composition comprises 1%-5% lysine, in free or salt form.

1.25 Any foregoing composition wherein the polyamine is lysine in free or salt form and the composition further comprises glutamic acid, in free or salt form, wherein the combined amount of lysine and glutamic acid is 1 to 10%; e.g., a combination of lysine and glutamic acid in a weight ratio of lysine:glutamic acid of 3:1 to 5:1, wherein the weight % is calculated on the basis of the weight of the free amino acids.

1.26 Any foregoing composition wherein the composition comprises lysine in the form of the hydrochloride salt.

1.27 Any foregoing composition wherein the composition comprises 3%-5% lysine hydrochloride.

1.28 Any foregoing composition further comprising glutamic acid, in free or salt form, 1.29 Any foregoing composition wherein the polyamine, in free or orally acceptable salt form, is lysine, and the composition further comprises glutamic acid, the lysine and the glutamic acid each being in free or orally acceptable salt form, in a total amount of 1 to 10%.

1.30 Any foregoing composition wherein the polyamine, in free or orally acceptable salt form is lysine, and the composition further comprises glutamic acid, each of the lysine and the glutamic acid being in free or orally acceptable salt form and in a weight ratio of lysine: glutamic acid of 3:1 to 5:1, weight being calculated on the basis of the free amino acid.

1.31 Any foregoing composition wherein the composition comprises a cationic active agent, e.g., a cationic antimicrobial agent.

1.32 Any foregoing composition wherein the composition comprises a cationic active agent, which is an antimicrobial agent, in an antimicrobially effective concentration.

1.33 Any foregoing composition wherein the composition comprises a cationic active agent selected from one or more of quaternary ammonium surfactants (such as cetyl pyridinium chloride (CPC), benzalkonium chloride, cetyl trimethylammonium bromide or chloride, didecyldimethylammonium chloride, benzethonium chloride), bisguanides (such as chlorhexidine digluconate), cationic amino acids (such as arginine), metal cations (such as zinc, calcium, or stannous ions), or combinations thereof, e.g.

1.34 Any foregoing composition wherein the composition is an oral care product, e.g., a mouthwash, and comprises an effective amount of an orally acceptable antimicrobial cationic active agent selected from one or more of quaternary ammonium surfactants (such as cetyl pyridinium chloride (CPC)), bisguanides (such as chlorhexidine digluconate), cationic amino acids (such as arginine), metal cations (such as zinc, calcium, or stannous ions), and combinations thereof; or 1.35 Any foregoing composition wherein the composition comprises a cationic active agent comprising a pyridinium surfactant, e.g., cetyl pyridinium chloride (CPC).

1.36 Any foregoing composition wherein the composition comprises a cationic active agent comprising chlorhexidine.

1.37 Any foregoing composition wherein the composition comprises a cationic active agent comprising arginine.

1.38 Any foregoing composition wherein the composition comprises a cationic active agent comprising zinc ions.

1.39 Any foregoing composition wherein the composition comprises a cationic active agent provided by an orally acceptable salt selected from zinc salts, stannous salts, pyridinium salts, and bisguanide salts.

1.40 Any foregoing composition wherein the composition comprises a cationic active agent provided by a salt selected from cetyl pyridinium chloride and chlorhexidine digluconate.

1.41 Any foregoing composition wherein the composition comprises a cationic active agent provided by a zinc salt, stannous salt or combination thereof.

1.42 Any foregoing composition wherein the effective amount of cationic active agent, in free or salt form, is present and comprises cetyl pyridinium chloride, in an amount of 0.05 to 0.1%, e.g., about 0.075%.

1.43 Any foregoing composition wherein the effective amount of cationic active agent, in free or salt form, is present and comprises chlorhexidine digluconate, in an amount of 0.1 to 0.2%, e.g., about 0.12%.

1.44 Any foregoing composition wherein the composition exhibits at least 50% separation after shaking and leaving the composition to stand for an hour; at least 60% separation after shaking and leaving the composition to stand for an hour; at least 70% separation after shaking and leaving the composition to stand for an hour; at least 80% separation after shaking and leaving the composition to stand for an hour; at least 90% separation after shaking and leaving the composition to stand for an hour; or at least 95% separation after shaking and leaving the composition to stand for an hour.

1.45 Any foregoing composition, wherein the composition has a viscosity of 10-40 cP; e.g., 15-35 cP; e.g., 20-30 cP.

1.46 Any foregoing composition comprising an antimicrobial phenolic compound, e.g., selected from *magnolia* extract compounds (e.g. magnolol or honokiol), phenol, cresols (e.g., thymol), halogenated (e.g., chlorinated or brominated) phenols (e.g. hexachlorophene, trichlorophenol, tribromophenol, or pentachlorophenol); or an antimicrobial halogenated di-phenyl compound, e.g., triclosan, or triclocarban.

1.47 Any foregoing composition wherein the composition comprises taurine, e.g., 0.3-3% taurine.

1.48 Any foregoing composition wherein the composition comprises greater than 40% water; e.g., greater than 50% water.

1.49 Any foregoing composition wherein the composition comprises 40% to 65% water; e.g., 50% to 60% water.

1.50 Any foregoing composition wherein the composition comprises one or more of a thickener, a buffer, a humectant, a surfactant, an abrasive, a sweetener, a flavorant, a pigment, a dye, an anti-caries agent, an anti-bacterial agent, a whitening agent, a desensitizing agent, a preservative, or a mixture thereof 1.51 Any foregoing composition wherein the composition contains a bluing agent, e.g., a blue dye or blue pigment, e.g., capable of imparting color to the composition and/or providing a whiter appearance to a yellow surface, for example the surface of a tooth 1.52 Any foregoing composition wherein the composition comprises a buffer wherein the buffer comprises sodium hydroxide.

1.53 Any foregoing composition wherein the composition comprises a humectant.

1.54 Any foregoing composition wherein the composition comprises a humectant, wherein the humectant is a mixture of glycerin, sorbitol, and propylene glycol.

1.55 Any foregoing composition wherein the composition comprises an anionic surfactant 1.56 Any foregoing composition wherein the composition comprises an abrasive.

1.57 Any foregoing composition wherein the composition comprises an abrasive, wherein the abrasive comprises silica.

1.58 Any foregoing composition wherein the composition comprises a sweetener.

1.59 Any foregoing composition wherein the composition comprises a sweetener, wherein the sweetener is sodium saccharin.

1.60 Any foregoing composition wherein the composition comprises a flavorant.

1.61 Any foregoing composition wherein the composition comprises a dye.

1.62 Any foregoing composition wherein the composition comprises an anti-caries agent.

1.63 Any foregoing composition wherein the composition comprises a fluoride ion source.

1.64 Any foregoing composition wherein the composition comprises a fluoride ion source, wherein the fluoride ion source is stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, or a mixture thereof.

1.65 Any foregoing composition wherein the composition comprises a whitening agent.

1.66 Any foregoing composition wherein the composition comprises a whitening agent, wherein the whitening agent is hydrogen peroxide.

1.67 Any foregoing composition wherein the composition comprises a desensitizing agent, a vitamin, a preservative, an enzyme, or a mixture thereof 1.68 Any foregoing composition wherein each of the anionic polymer, the nonionic polymer, the polyamine, and the cationic active agent (if any) are each orally acceptable, e.g., safe for administration to the oral cavity of a human at relevant concentrations.

1.69 Any foregoing composition wherein the composition is a mouthwash, toothpaste, tooth gel, tooth powder, non-abrasive gel, foam, mouth spray, lozenge, oral tablet, dental implement, or pet oral care product.

1.70 Any foregoing composition wherein the composition is a mouthwash, e.g., wherein all ingredients of the composition are orally acceptable, e.g., safe and palatable for administration to the oral cavity of a human at relevant concentrations.

1.71 Any foregoing composition which is biphasic, wherein one phase comprises at least 90% of the orally acceptable acidic polymer, the at least one polyphosphate, the orally acceptable cationic active agent (where present), and the lysine or polylysine, and the other phase comprises at least 90% of the orally acceptable nonionic polymer.

1.72 Any foregoing composition which comprises less than 5%, e.g., less than 2% of hydrophobic ingredients.

1.73 Any foregoing composition which is essentially oil-free, apart from flavoring agents.

1.74 Any of Composition 1-1.71 further comprising an oil phase, e.g., comprising mineral oil.

1.75 Any foregoing composition having a pH between the isoelectric point of the acidic polymer and the isoelectric point of the polyamine compound.

1.76 Any foregoing composition having a pH of 4.6 to 8.0 (i.e., 6.0-6.5).

1.77 Any foregoing composition wherein the composition comprises an anionic surfactant, wherein the anionic surfactant is selected from sodium laureth sulfate and sodium lauryl sulfate.

1.78 Any foregoing composition further comprising sodium lauryl sulfate in an amount of up to 1%.

1.79 Any foregoing composition further comprising sodium lauryl sulfate, e.g., 0.1-1.5%.

1.80 Any foregoing composition which is a mouthwash comprising 1-2%, e.g., about 2.5% phosphate/acrylate co-polymer having a molecular weight of 20 to 30 kDa; 0.05-0.1%, e.g., about 0.075% cetyl pyridinium chloride; 0.5-2%, 3-6%, e.g., 4-5%, total polyphosphates (i.e., sodium tripolyphosphate or a combination of sodium tripolyphosphate and sodium acid pyrophosphate); 3-5%, e.g., about 4% lysine; 5-7%, e.g., about 6% polyethylene glycol having molecular weight of 8-12 kDa, e.g. about 10 kDa, and 50-60% water.

1.81 Any foregoing composition, wherein a first phase comprises:
a) a nonionic polymer, and
b) water; and a second phase comprises:
a) an acidic polymer;
b) at least one polyphosphate;
c) a stabilizing amount of a polyamine compound; and
d) water,
wherein the first phase is a top phase and the second phase is a bottom phase after separation.

1.82 Any foregoing composition wherein the composition has any one or more or all of the following features:
  a) the acidic polymer comprises a combination of a phosphate/acrylate co-polymer in a total amount of 1% to 5%; e.g., about 2%;
  b) the nonionic polymer comprises a combination of (i) polyethylene glycol having an average molecular weight of 5 kDa to 35 kDa, e.g., PEG 8 k or PEG 35 k, and (ii) poloxamer 407, in a total amount of 0.1-2%; e.g., 4-6% polyethylene glycol and 0.5-1.5% poloxamer;
  c) the polyphosphate comprises sodium tripolyphosphate in an amount of 1-6% (e.g., 4-5%); or a combination of sodium tripolyphosphate and sodium acid pyrophosphate each present in an amount of about 0.1-4% (e.g., 2-3%);
  d) the polyamine, in free or salt form, is lysine;
  e) the water is present in an amount of 50-60% N; and
  f) a cationic active agent is present in an effective amount, in free or orally acceptable salt form and comprises cetyl pyridinium chloride, in an amount of 0.05 to 0.1%0, e.g., about 0.075%,
  wherein the composition is a mouthwash, further comprising humectant, e.g., propylene glycol, glycerin and sorbitol in an amount of 20-40%, and about 1%, flavoring, sweetener, preservative (e.g. sodium benzoate or potassium sorbate in an amount of 0.04%-0.06%), and dye (e.g., Blue Dye #1)
  wherein all ingredients are orally acceptable, e.g., safe and palatable at relevant concentrations for use in a mouthwash;
  wherein all amounts are by weight of the total composition.

Further claimed is the use of a polyamine, e.g., lysine, in free or orally acceptable salt form, to stabilize an aqueous biphasic formulation, e.g., according to any of Composition 1, et seq., e.g. comprising an acidic polymer, a nonionic polymer, and optionally an effective amount of a cationic active agent, in free or orally acceptable salt form; for example, use in any of the foregoing Compositions 1, et seq.

As used herein, an "oral care composition" refers to a composition for which the intended use can include oral care, oral hygiene, or oral appearance, or for which the intended method of use can comprise administration to the oral cavity. The term "oral care composition" thus specifically excludes compositions which are highly toxic, unpalatable, or otherwise unsuitable for administration to the oral cavity. In some embodiments, an oral care composition is not intentionally swallowed, but is rather retained in the oral cavity for a time sufficient to affect the intended utility. The oral care compositions as disclosed herein may be used in nonhuman mammals such as companion animals (e.g., dogs and cats), as well as by humans. In some embodiments, the oral care compositions as disclosed herein are used by humans. Oral care compositions include, for example, dentifrice and mouthwash. In some embodiments, the disclosure provides mouthwash formulations.

As used herein, "orally acceptable" refers to a material that is safe and palatable at the relevant concentrations for use in an oral care formulation, such as a mouthwash or dentifrice.

As used herein, "orally acceptable carrier" refers to any vehicle useful in formulating the oral care compositions disclosed herein. The orally acceptable carrier is not harmful to a mammal in amounts disclosed herein when retained in the mouth, without swallowing, for a period sufficient to permit effective contact with a dental surface as required herein. In general, the orally acceptable carrier is not harmful even if unintentionally swallowed. Suitable orally acceptable carriers include, for example, one or more of the following: a thickener, a buffer, a humectant, a surfactant, an abrasive, a sweetener, a flavorant, a pigment, a dye, an anti-caries agent, an anti-bacterial, a whitening agent, a desensitizing agent, a vitamin, a preservative, an enzyme, and mixtures thereof.

As used herein, "cationic active agent" means an agent which is cationic in aqueous solution at neutral pH and which provides some benefit, e.g. antimicrobial activity. In an oral care formulation, the cationic active agent may provide anti-gingivitis, anticavity and/or antierosion activity to the teeth, gums, or oral cavity. While in aqueous formulation, the agent will generally be in solution, but it may be introduced to the formulation formulated in free or salt form. In certain embodiments, for example in certain oral care formulations, the cationic active agent may be selected from one or more of quaternary ammonium surfactants (such as cetyl pyridinium chloride (CPC)), bisguanides (such as chlorhexidine digluconate), cationic amino acids (such as arginine), metal cations (such as zinc, calcium, or stannous ions), or combinations thereof.

As used herein, "acidic polymer" means a polymer comprising monomers bearing acidic groups, for example carboxy and/or phosphate groups, for example selected from one or more of synthetic anionic linear or branched polycarboxylates and phosphate/acrylate co-polymers and mixtures thereof. The acidic polymer should have a relatively low isoelectric point, e.g., pH 5 or less. The appropriate molecular weight will vary depending on the specific polymer, the degree of crosslinking or branching, and the proportion of acidic functional groups, but in general, the molecular weight is greater than 5000 g/mol. In various embodiments, the acidic polymer could be in a linear or nonlinear (i.e. branched) form or a mixture of linear and branched forms, the backbone or side chains could contain various hydrophobic moieties such as methyl methacrylate monomers, alkane chains, etc., and/or as hydrophilic uncharged moieties such as PEG or PPG, as well as moieties bearing acidic functional groups. Examples of acidic polymers include synthetic anionic linear polycarboxylates, phosphate/acrylate co-polymers, and combinations thereof. The acidic polymer can be made up of copolymers or homopolymers of acidic functional monomers or mixtures thereof.

As used herein, a "nonionic polymer" is a water soluble polymer which does not form an ionic species at relevant pH, e.g., between pH 3 and 10, for example in certain embodiments selected from one or more poly(alkylene oxide) polymers, e.g., selected from polyethylene glycols (PEG), polypropylene glycols (PPG), poloxamers (block co-polymers of PEG and PPG), random copolymers of PEG and PPG, and mixtures thereof. In some embodiments, the nonionic polymer has a molecular weight of at least 3000D, e.g., 6 kDa to 250 kDa. The molecular weight may vary depending on the particular type of polymer, the degree of branching, if any, and the concentration used. Experiments with PEG having molecular weight between 6 kDa and 35 kDa, for example, showed that at lower concentrations, e.g., for a 3% concentration in a particular combination with other ingredients, a higher molecular weight material, e.g. 35 kDa, was needed to form the biphasic system, but at formulations having higher levels of PEG, a PEG having a lower molecular weight, e.g., 8 kDa could support a biphasic system. In particular embodiments, the nonionic polymer comprises a mixture of (i) polyethylene glycol (MW 5 kDa-35 kDa) and (ii) poloxamer (i.e., an ethylene oxide/propylene oxide block copolymer), e.g., poloxamer 407, which is a triblock copolymer consisting of a central hydrophobic block of polypropylene glycol flanked by two hydrophilic blocks of polyethylene glycol, wherein the approximate length of the two PEG blocks is about 101 repeat units while the approximate length of the propylene glycol block is about 56 repeat units, available commercially for example as Pluronic F127 (BASF).

As used herein "polyamine compound" means a molecule having at least two primary or secondary amine groups, for example having an isoelectric point of greater than pH 8.5, for example pH 9-10. Examples of polyamines include ethylene diamine, lysine, or histadine, as well as polymers such as Lupasol P, which is a polyethylenimine. The polyamine must be safe for its intended use. Where the composition is an oral care composition, the polyamine must be orally acceptable. The polyamine may be provided in free or acid addition salt form. In certain embodiments the polyamine compound is lysine.

As used herein "polyphosphate" refers to one or more compounds having a chain of two or more phosphate anions, which are present in an amount to facilitate separation of the two distinct aqueous phases. Examples of suitable polyphosphates are alkali pyrophosphates or alkali polyphosphates. For example, the polyphosphates according to this disclosure may be sodium tripolyphosphate, tetrasodium pyrophosphate, sodium acid pyrophosphate, tetrapotassium pyrophosphate, sodium hexametaphosphate or combinations thereof. In various embodiments, the polyphosphate used comprises a mixture of sodium tripolyphosphate and sodium acid pyrophosphate. The sodium tripolyphosphate and sodium acid pyrophosphate may be present in a ratio of 2:1 to 1:2. In some embodiments, the sodium acid pyrophosphate may also be used to adjust the pH of the composition.

As used herein, "biphasic" refers to stable liquid compositions which contain at least two distinct homogeneous phases, having different densities, such that the phases are separate at rest. The phases may be readily mixed by shaking but will then re-separate over a short period, e.g., less than half an hour. In certain embodiments, the term excludes gels, emulsions, microemulsions, and homogeneous solutions. In certain embodiments, these formulations differ from conventional biphasic formulations in that both phases are aqueous, rather than one phase being hydrophobic and the other hydrophilic.

As used herein, "isoelectric point" is the pH in aqueous solution where the molecule has no net charge. To form the biphasic system, three components are needed, two of which are charged—the polyamine compound, e.g. lysine, and the acidic polymer, e.g., DV8801. The isoelectric point of lysine, for example, occurs at pH 9.7 due to its two amines and one carboxylic acid (at this point only one amine is positive and the acid is negative). At every other pH, Lys contains some degree of charge whether overall positive (<pH 9.7, both amines are protonated) or negative (>pH 9.7, both amines are depronated—neutral—and the acid group has a negative charge). The acidic polymer, e.g., DV8801, will only have an isoelectric point at low pH<5 at the point where the carboxylates are all protonated resulting in a net 0 charge. The biphasic system exists between the isoelectric points of the necessary materials.

As used herein, "phosphate/acrylate co-polymer" refers to a polymer made up of acrylate monomers and phosphate-bearing monomers, e.g., a co-polymerized product of a mixture of acrylic acid, methacrylic acid, and a mixture of compounds of Formula 1:

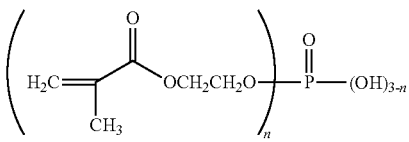

wherein n is 0, 1 or 2. In some embodiments, the phosphate/acrylate co-polymer is a co-polymerized product of a mixture of acrylic acid, methacrylic acid, and 2-hydroxyethyl methacrylate phosphates of Formula 1, comprising acrylic acid in a molar percentage of 80-90%, e.g., about 85%; methacrylic acid in a molar percentage of 5-15%, e.g., about 11%, and hydroxyethyl methacrylate phosphates of Formula 1 in a molar percentage of 2-6%, e.g., about 4%. In some embodiments, the phosphate/acrylate co-polymer has an average molecular weight of from 10 to 40 kDa, e.g., 20 to 30 kDa. Phosphate/acrylate co-polymers as described include commercially available polymers, e.g. DV8801 (Rhodia), sometimes referred to herein as DV. The phosphate side group of a phosphate/acrylate co-polymer, as disclosed herein, may function as an anchor to deposit the co-polymer onto the tooth surface thereby forming a physical layer on the tooth surface that may inhibit staining and/or biofilm formation. For example, in a particular embodiment (the embodiment used in the Examples below), the phosphate/acrylate copolymer is a random copolymer having a weight average molecular weight of about 20,000 to 30,000 grams per mole that is the copolymerized product of a mixture of, in the relative amounts set forth in Table 1 below, 2-hydroxyethy methacrylate phosphates, acrylic acid, and methacrylic acid.

TABLE 1

| Monomer Name and Structure | Monomer Weight Ratio (weight %) | Monomer Molar Ratio (Mole %) |
|---|---|---|
| 2-hydroxyethyl methacylate phosphates | 11 | 4 |
| mixture of n = 0, n = 1, and n = 2 | | |
| acrylic acid | 75 | 85 |

TABLE 1-continued

| Monomer Name and Structure | Monomer Weight Ratio (weight %) | Monomer Molar Ratio (Mole %) |
|---|---|---|
| methacrylic acid 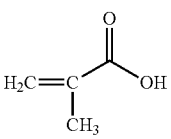 | 14 | 11 |

As used herein, "synthetic anionic linear polycarboxylate" refers to a polymer synthesized by using an olefinically or ethylenically unsaturated carboxylic acid that contains an activated carbon-to-carbon olefinic double bond and at least one carboxyl group. The acid contains an olefinic double bond that readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrilacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other olefinic monomers copolymerizable with such carboxylic monomers include vinyl acetate, vinyl chloride, dimethyl maleate and the like. The synthetic anionic linear polycarboxylate is mainly a hydrocarbon with optional halogen and O-containing substituents and linkages as present in for example ester, ether, and OH groups. The copolymers preferably contain sufficient carboxylic salt groups for water-solubility. The terms "synthetic" and "linear" do not include known thickening or gelling agents comprising carboxymethylcellulose and other derivatives of cellulose and natural gums, nor Carbopols having reduced solubility due to cross-linkages.

As used herein, a "tartar control agent" refers to a compound or a mixture of compounds that inhibit the formation of tartar, a mixture of calcium phosphates on organic matrices, and/or the deposition of plaque on teeth to form tartar (calculus).

As used herein, "chemical stain" refers to a discoloration of a surface, e.g., a dental surface caused by adsorption or absorption of a colored agent on or into the surface, or caused by chemical reaction of material of the surface (e.g., dental enamel) with a colored or noncolored agent contacting the surface. "Chemical staining" herein means formation and/or development of a chemical stain.

As used herein, "dental surface" refers to a surface of a natural tooth or a hard surface of artificial dentition including a crown, cap, filling, bridge, dental implant and the like. In some embodiments, the dental surface is a natural tooth.

Oral Care Compositions:

In some embodiments the compositions are oral care compositions, in accordance with Composition 1, et seq. for example mouthwashes. Any of the compositions of Composition 1, et seq. is suitable for oral care use, provided the ingredients are orally acceptable. In some embodiments, the mouthwash of Composition 1 comprises an effective amount of an orally acceptable cationic active agent, which is an antimicrobial, antigingivitis, anti-erosion and/or anti-caries agent, e.g. a cationic active agent selected from one or more of quaternary ammonium surfactants (such as cetyl pyridinium chloride (CPC)), bisguanides (such as chlorhexidine digluconate), cationic amino acids (such as arginine), metal cations (such as zinc, calcium, or stannous ions), or combinations thereof. The orally acceptable cationic active agent may be present in an effective amount, for example an antimicrobial, antigingivitis, anti-erosion and/or anti-caries amount. The precise amount will depend on the particular active agent and the condition to be treated or prevented, but in various embodiments, antimicrobially effective levels of CPC in a mouthwash would include amounts from 0.05 to 0.1%, e.g., about 0.075%; antimicrobially effective levels of chlorhexidine digluconate in a mouthwash would include amounts from 0.1-0.2%, e.g., about 0.12%; anti-erosion or anti-microbial levels of metal cations such as zinc (e.g., zinc citrate or other soluble salt) or stannous (e.g., stannous fluoride and/or stannous chloride) would be on the order of 100-1500 ppm.

The oral care composition used in the present disclosure comprise significant levels of water. Water employed in the preparation of commercial oral compositions should be deionized and free of organic impurities. The amount of water in the compositions includes the free water that is added plus that amount which is introduced with other materials.

Mouthwashes frequently contain significant levels of ethanol, which is often needed to solubilize essential oils and to prevent bacterial contamination. High levels of ethanol may be undesirable, because in addition to the potential for abuse by ingestion, the ethanol may exacerbate conditions like xerostoma. Accordingly, in some embodiments, the oral care compositions of the invention are substantially free of ethanol, e.g., contain less than 1% ethanol.

Humectants can enhance the viscosity, mouthfeel, and sweetness of the product, and may also help preserve the product from degradation or microbial contamination. Suitable humectants include edible polyhydric alcohols such as glycerin, sorbitol, xylitol, propylene glycol as well as other polyols and mixtures of these humectants. Sorbitol may in some cases be provided as a hydrogenated starch hydrolysate in syrup form, which comprises primarily sorbitol (the product if the starch were completely hydrolyzed to glucose, then hydrogenated), but due to incomplete hydrolysis and/or presence of saccharides other than glucose, may also include other sugar alcohols such mannitol, maltitol, and longer chain hydrogenated saccharides, and these other sugar alcohols also function as humectants in this case. In some embodiments, humectants are present at levels of 5% to 40%, e.g., 20%0 to 30% by weight.

Flavorings for use in the present invention may include extracts or oils from flavorful plants such as peppermint, spearmint, cinnamon, wintergreen, and combinations thereof, cooling agents such as menthol, methyl salicylate, and commercially available products such as OptaCool® from Symrise, as well as sweeteners, which may include polyols (which also function as humectants), saccharin, acesulfame, aspartame, neotame, *stevia* and sucralose.

Further provided is a method (Method A) for the treatment and/or inhibition of a chemical stain, plaque, and/or tartar on a dental surface, comprising shaking the composition according to any of Composition 1, et seq. to disperse the phases and contacting the dental surface therewith.

Further provided herein is Method A as follows:
- A.1 Method A wherein the composition is Composition 1, et seq., e.g., wherein the ingredients are orally acceptable, e.g. wherein the composition is a mouthwash.
- A.2 Method A or A.1 wherein the method is for the treatment of a chemical stain, plaque, and/or tartar on the dental surface.
- A.3 Method A.2 wherein the method is for the treatment of a chemical stain on the dental surface.
- A.4 Method A.2 wherein the method is for the treatment of plaque on the dental surface.
- A.5 Method A.2 wherein the method is for the treatment of tartar on the dental surface.
- A.6 Method A or A.1 wherein the method is for the inhibition of a chemical stain, plaque, and/or tartar on the dental surface.
- A.7 Method A.6 wherein the method is for the inhibition of a chemical stain on the dental surface.
- A.8 Method A.6 wherein the method is for the inhibition of plaque on the dental surface.
- A.9 Method A.6 wherein the method is for the inhibition of tartar on the dental surface.
- A.10 Method A or A.1-A.9 wherein the dental surface is a human tooth.
- A.11 Method A or A.1-A.10 wherein the composition is contacted with the dental surface by brushing.

Further provided is a method (Method B) for the treatment and/or inhibition of gum disease comprising shaking the composition according to any of Composition 1, et seq. to disperse the phases and contacting the oral cavity therewith.

Further provided herein is Method B as follows:
- B.1 Method B wherein the composition is Composition 1, et seq., e.g., wherein the ingredients are orally acceptable, e.g. wherein the composition is a mouthwash.
- B.2 Method B or B.1 wherein the method is for the treatment of gum disease.
- B.3 Method B, B.1, or B.2 wherein the gum disease is gingivitis.
- B.4 Method B, B.1, or B wherein the gum disease is periodontitis.
- B.5 Method B or B.1 wherein the method is for the inhibition of gum disease.
- B.6 Method B, B.1, or B.5 wherein the gum disease is gingivitis.
- B.7 Method B, B.1, or B.5 wherein the gum disease is periodontitis.
- B.8 Method B or B.1-B.7 wherein the oral cavity is a human oral cavity.
- B.9 Method B or B.1-B.8 wherein the composition is contacted with the oral cavity by brushing.

Further provided is a method (Method C) for the treatment and/or inhibition of halitosis comprising shaking the composition according to any of Composition 1, et seq. to disperse the phases and contacting the oral cavity therewith.

Further provided herein is Method C as follows:
- C.1 Method C wherein the composition is Composition 1, et seq., e.g., wherein the ingredients are orally acceptable, e.g. wherein the composition is a mouthwash.
- C.2 Method C or C.1 wherein the oral cavity is a human oral cavity.
- C.3 Method C, C.1, or C.2 wherein the composition is contacted with the oral cavity by brushing.

Further provided is a method (Method D) for inhibiting biofilm formation on a dental surface comprising shaking the composition according to any of Composition 1, et seq. to disperse the phases and contacting the dental surface therewith.

Further provided herein is Method D as follows:
- D.1 Method D wherein the composition is Composition 1, et seq., e.g., wherein the ingredients are orally acceptable, e.g. wherein the composition is a mouthwash.
- D.2 Method D or D.1 wherein the dental surface is a human tooth.
- D.3 Method D, D.1, or D.2 wherein the composition is contacted with the dental surface by brushing.

Further provided is a method (Method E) for treating and/or inhibiting bacteria from sticking together and growing into bigger colonies in an oral cavity comprising shaking the composition according to any of Composition 1, et seq. to disperse the phases and contacting the dental surface therewith and contacting the oral cavity therewith.

Further provided herein is Method E as follows:
- E.1 Method E wherein the composition is Composition 1, et seq., e.g., wherein the ingredients are orally acceptable, e.g. wherein the composition is a mouthwash.
- E.2 Method E or E.1 wherein the oral cavity is a human oral cavity.
- E.3 Method E, E.1, or E.2 wherein the composition is contacted with the oral cavity by brushing.

Further provided are Compositions 1, et seq. for use in any of Methods A-E.

As used herein, "inhibition" refers to reduction of stains that would otherwise form or develop subsequent to the time of the treatment. Such inhibition can range from a small but observable or measurable reduction to complete inhibition of subsequent staining, by comparison with an untreated or placebo-treated dental surface.

Where the dental surface is substantially free of chemical stains, Method A, e.g., A.1-A.11, is effective to inhibit formation and development of new chemical stains, as can occur for example by oral use of tobacco products (including smoking) or by drinking tea, coffee, red wine, or coke, subsequent to treatment according to the method. Where the dental surface already possesses some degree of chemical staining, Method A, e.g., A.1-A.11, is effective to inhibit further development of the existing stain. In some embodiments, the Method A, e.g., A.1-A.11, can remove, partially or completely, an existing chemical stain as well as inhibit subsequent staining.

EXAMPLES

Example 1—Formulation

Compositions were formulated having combinations of Rhodia DV8801 (a.k.a. Mirapol 8801) (DV), lysine (Lys), sodium tripolyphosphate (STPP and polyethylene glycol having a molecular weight of about 8,000 daltons. The formulations are mixed together and result in biphasic solutions with a PEG concentrated layer on top, and a DV-Lys concentrated layer on the bottom. Aqueous biphasic mouthwash formulation is prepared with the following ingredients:

TABLE 2

Biphasic mouthwash formulations

| Material | Model Formulation (wt. %) | Comparative Formulation |
| --- | --- | --- |
| Water | q.s. | q.s. |
| Poloxamer | 0.1-2 | 0.1-2 |
| Lysine | 2-6 | 2-6 |
| Polyethylene Glycol (8,000D) | 3-6 | 3-6 |
| Rhodia DV8801 (in 41% solution) | 0.1-5 | 0.1-5 |
| Methyl Vinyl Ether/Maleic Anhydride Copolymer (in 16% solution) | 0 | 6 |

TABLE 2-continued

Biphasic mouthwash formulations

| Material | Model Formulation (wt. %) | Comparative Formulation |
|---|---|---|
| Cetyl Pyridinium Chloride | 0.001-1 | 0.001-1 |
| Potassium Sorbate | 0.01-1 | 0.01-1 |
| Glycerin | 5-15 | 5-15 |
| Sorbitol | 5-15 | 5-15 |
| Propylene Glycol | 5-10 | 5-10 |
| Sodium Tripolyphosphate (STPP) | 0.1-8 | 0 |
| Flavorants and Colorants | 0.1-1 | 0.1-1 |

The Model Formulation and the Comparative Formulation were created in the same way with identical ingredients. However, the comparative formulation was made having a methyl vinyl ether/maleic anhydride copolymer in an amount of 6 wt. % and the model formulation contained 5 wt. % STPP.

Example 2—Formulation Derivations

Derivatives of the Model Formulation as described in Example 1 were created to test the effect varying the STPP and Lys levels had on separation of top and bottom layers. The results are summarized below in Table 3.

TABLE 3

Impact of STPP/Lys levels on phase separation

| Formula | STPP | Lys | Separation |
|---|---|---|---|
| 1 | 5 | 4 | 30/70 |
| 2 | 5 | 3.5 | 40/60 |
| 3 | 5 | 3 | 40/60 |
| 4 | 5 | 2.5 | 40/60 |
| 5 | 4.5 | 4 | 45/55 |
| 6 | 4.5 | 3.5 | 40/60 |
| 7 | 4.5 | 3 | 50/50 |
| 8 | 4.5 | 2.5 | 50/50 |
| 9 | 4.5 | 2 | 55/45 |
| 10 | 4 | 4 | 45/55 |
| 11 | 4 | 3.5 | 45/55 |
| 12 | 4 | 3 | 50/50 |
| 13 | 4 | 2.5 | 50/50 |
| 14 | 4 | 2 | 70/30 |
| 15 | 3.5 | 4 | 60/40 |
| 16 | 3.5 | 3.5 | 60/40 |
| 17 | 3.5 | 3 | 60/40 |
| 18 | 3.5 | 2.5 | 65/35 |
| 19 | 3.5 | 2 | No phase separation observed |

As shown above, the STPP/Lys formulations generally favored a smaller top phase. However, iterations 14-18 showed a larger top phase as a result of decreased STPP/Lys use levels, and since PEG was kept constant in all formulations in Table 3. These samples exhibited increased separation time as a result. Iteration 19 did not separate throughout the entire test period as a result of significantly decreased STPP/Lys levels.

Table 4 below details derivatives of the Model Formulation described in Example 1, but varies the amount of DV and STPP. The pH was also varied between various levels of acidity. DV concentrations are listed below as isolated weight percentages, as opposed to the use level of a 41% solution (i.e., as in Table 2). Viscosity measurements were performed on a Brookfield Low Viscosity Instrument, using spindle #2 and RPM=20.

TABLE 4

Effect of DV/STPP/pH on separation time and viscosity

| Formula | DV | STPP | pH | Separation (Top/Bottom) | Viscosity (cP) |
|---|---|---|---|---|---|
| Comparative Formulation | 1 | 0 | 6.4 | 60/40 | 40.9 |
| 1 | 1.25 | 3 | 4.6 | N/A | — |
| 2 | 1.25 | 3 | 4 | 52/48 | 22.7 |
| 3 | 1.25 | 5 | 4.6 | 28/72 | 24.7 |
| 4 | 1.25 | 5 | 4 | 26/74 | 25.7 |
| 5 | 0.5 | 3 | 4.6 | N/A | — |
| 6 | 0.5 | 3 | 4 | N/A | — |
| 7 | 0.5 | 5 | 4.6 | 22/78 | 22.3 |
| 8 | 0.5 | 5 | 4 | 29/71 | 23.8 |
| 9 | 0.875 | 4 | 5.3 | 32/68 | 23.4 |
| 10 | 1 | 3.75 | 4.6 | 37/63 | 23.1 |
| 11 | 1 | 3.75 | 4 | 11/89 | 23.4 |
| 12 | 1 | 5 | 4.6 | 31/69 | 25.1 |
| 13 | 1 | 5 | 4 | 10/90 | 23.8 |
| 14 | 0.75 | 3.75 | 4.6 | 33/67 | 22.5 |
| 15 | 0.75 | 3.75 | 4 | 5/95 | 22.1 |
| 16 | 0.75 | 5 | 4.6 | 30/70 | 23.2 |
| 17 | 0.75 | 5 | 4 | 5/95 | 22.9 |
| 18 | 0.875 | 3.875 | 5.3 | 34/66 | 22.7 |

As shown above, most formulations showed phase separation. In fact, phase separation was observed at all tested pH values (i.e., in formulations having a pH of 4, 4.6 and 5.3). Further, each of the tested compositions showed superior viscosities in comparison with the Comparative Formulation.

Table 5 details derivatives of the Model Formulation described in Example 1, but varies the amount of DV, STPP and PEG. The pH was also varied between various levels of acidity. Separation progress was recorded at 30 minutes and 60 minutes in terms of percent separation. DV concentrations are listed below as isolated weight percentages, as opposed to the use level of a 41% solution (i.e., as in Table 2). Viscosity measurements were performed on a Brookfield Low Viscosity Instrument, using spindle #2 and RPM=20.

TABLE 5

Formulation variations and their impact on separation level, separation time and viscosity

| Formula | DV | STPP | PEG | pH | Sep. (T/B) | Separation % 30 min | Separation % 60 min | Viscosity (cP) |
|---|---|---|---|---|---|---|---|---|
| 1 | 1 | 5 | 5 | 6 | 36/64 | 55 | 87 | 31.9 |
| 2 | 1 | 5 | 5 | 5.25 | 40/60 | 40 | 80 | 30.2 |
| 3 | 1 | 5 | 4.5 | 6 | 33/67 | 46 | 82 | 29.8 |
| 4 | 1 | 5 | 4.5 | 5.25 | 40/60 | 18 | 55 | 28.3 |
| 5 | 1 | 4 | 5 | 6 | 44/56 | 29 | 67 | 32.8 |
| 6 | 1 | 4 | 5 | 5.25 | 55/45 | 0 | 23 | 26.2 |
| 7 | 1 | 4 | 4.5 | 6 | 33/67 | 22 | 42 | 28.7 |
| 8 | 1 | 4 | 4.5 | 5.25 | 37/63 | 0 | 0 | 22.7 |
| 9 | 0.5 | 5 | 5 | 6 | 33/67 | 40 | 86 | 27.5 |
| 10 | 0.5 | 5 | 5 | 5.25 | 37/63 | 18 | 42 | 26.1 |
| 11 | 0.5 | 5 | 4.5 | 6 | 33/67 | 36 | 82 | 25.3 |
| 12 | 0.5 | 5 | 4.5 | 5.25 | 33/67 | 17 | 33 | 24 |
| 13 | 0.5 | 4 | 5 | 6 | 37/63 | 0 | 20 | 23.8 |
| 14 | 0.5 | 4 | 5 | 5.25 | N/A | — | — | 24.4 |
| 15 | 0.5 | 4 | 4.5 | 6 | 28/72 | 0 | 26 | 24.3 |
| 16 | 0.5 | 4 | 4.5 | 5.25 | N/A | — | — | 21.6 | pH Range

As shown in both Tables 4 and 5, a major benefit provided by the formulations is that the addition of phosphate salts allows for phase separation to occur at a wide pH range. For example, the aqueous biphasic system of the Comparative Formulation described in Example 1 can only separate between pH 5.5-8.5. It is only in this narrow range that charge complexation between the positively charged Lys and negatively charged acidic polymers occurs. Without being bound to theory, it is believed that at more acidic pH than this range, the acidic polymers are protonated and lose their charge; and at more basic pH the amines on Lys are depronated and lose their charge. Generally, the $pK_A$ of phosphates are significantly lower (about $pK_A$ 2) than a carboxylate group on DV or a copolymer of methyl vinyl ether/maleic anhydride (about $pK_A$ 5), allowing for biphasic system to form at lower pH. As shown in Table 4, formulations were shown to form a two-phase separation at a pH as low as 4. It is noted that the contribution of DV is likely negligible at this pH because it is expected to exist primarily in its protonated form. As such, the low-pH two phase system is likely dominated by a phosphate-Lys interaction.

Separation Time

A further benefit of using phosphates for biphasic systems is that the separation time is significantly decreased. The Comparative Formulation discussed in Example 1 showed a separation time longer than 4 hours.

Table 5 lists the separation factor at 30 and 60 minutes after shaking. The separation factor is defined as the percentage of discrete bottom phase formation relative to the final separation. For example, if a final separation is 50% bottom phase, and after 60 min, 40% of the bottle is discretely bottom phase, the separation factor is 40%/50%× 100=80% separated at 60 minutes.

The results indicate that generally higher phosphate use levels resulted in faster separation times. Formulations 1-3, 9, and 11 of Table 5 showed greater than 80% separation after 60 minutes. Each of these formulations contained either 4.5 or 5% PEG 8000 and 5% STPP. Formulas 6, 8, 13, and 15 were by far the slowest separators, indicating that those formulations having lower levels of STPP and DV were not able to separate effectively.

Example 3—pH Adjustment of Formulations

Given the high level of STPP in this new formulation, a high level of conventional pH adjustment agents such as citric acid is needed to adjust the pH to appropriate levels (i.e., pH 5-7). It was found that a combination of sodium acid pyrophosphate (SAPP) and STPP can be used to attenuate the pH and eliminate the need for large quantities of conventional pH adjustment agents. Table 6 below exhibits the pH response as a function of 5 wt. % total phosphate salt solution that also contains 1 wt. % DV and 4 wt. % Lys. The phosphate salts comprise a combination of STPP and SAPP to equal a total of 5 wt. %. A pH of 5.75 can be achieved from a combination of 1 DV, 4 Lys, 3 STPP and 2 SAPP.

TABLE 6 pH adjustment of formulations with SAPP

| SAPP/STPP (wt. %) | pH |
|---|---|
| 4/1 | 4.95 |
| 3/2 | 5.35 |
| 2.5/2.5 | 5.5 |
| 2/3 | 5.75 |
| 1.75/3.25 | 6.05 |
| 1.5/3.5 | 6.2 |
| 1.25/3.75 | 6.35 |
| 1/4 | 6.5 |

Samples 2, 3, 9, and 11 from Table 5, which were shown to have superior separability and viscosity products, were reformulated to contain a combination of SAPP/STPP and have a pH of 5.5-5.6. The results are listed in Table 7. As shown below, most samples showed better separation times, incrementally faster separation time and slightly lower viscosity.

TABLE 7

Selected formulations adjusted with SAPP

| For-mula | DV | STPP/SAPP | PEG | Sep. (T/B) | Separation % 30 min | Separation % 60 min | Viscosity (cP) |
|---|---|---|---|---|---|---|---|
| 2 | 1 | 2.5/2.5 | 5 | 34/66 | 58 | 93 | 26.6 |
| 3 | 1 | 2.5/2.5 | 4.5 | 33/67 | 48 | 90 | 25.6 |
| 9 | 0.5 | 2.5/2.5 | 5 | 36/64 | 45 | 79 | 24.2 |
| 11 | 0.5 | 2.5/2.5 | 4.5 | 30/70 | 23 | 52 | 23.8 |

Example 4—Formulations Having High Concentrations of DV

A series of formulations having DV at higher use level and a combination of STPP/SAPP were created for evaluation of separation and viscosity. As shown below in Table 8, it was found that generally, the greater the use level of DV, the higher the viscosity became. The results also showed a relationship between the separation time and the levels of DV and STPP/SAPP. A faster separation time resulted when higher levels of DV and generally lower levels of STPP/SAPP were used.

TABLE 8

Formulations having high concentrations of DV

| Formula | DV | STPP | Sep. (T/B) | Separation % 30 min | Separation % 60 min | Viscosity (cP) |
|---|---|---|---|---|---|---|
| 1 | 1.25 | 4 | 53/47 | 27 | 64 | 27.6 |
| 2 | 1.5 | 4 | 60/40 | 49 | 98 | 32.8 |
| 3 | 1.5 | 3 | 40/60 | 19 | 27 | 27.9 |
| 4 | 1.75 | 4 | 39/61 | 9 | 56 | 30.4 |
| 5 | 1.75 | 3 | 49/51 | 29 | 96 | 36.9 |
| 6 | 1.75 | 2 | 59/41 | 14 | 66 | 30.7 |
| 7 | 2 | 4 | 37/63 | 18 | 64 | 32.1 |
| 8 | 2 | 3 | 46/54 | 33 | 96 | 33.7 |
| 9 | 2 | 2 | 54/46 | 36 | 94 | 35.1 |

Example 5—Antibacterial Efficacy of

Studies were carried out to analyze the antibacterial efficacy of the discussed biphasic solutions containing DV, Lysine, STPP, SAPP and PEG. Three separate compositions were prepared, and are summarized in Table 9 below. Composition A and Composition B are identical, except that Composition B does not contain cetyl pyridinium chloride. Composition C is similar to Composition A, except that it contains varied amounts of STPP, SAPP and DV. Tests were also carried out against a commercial formulation.

TABLE 9

Exemplary Formulations

| Material | Composition A | Composition B | Composition C |
|---|---|---|---|
| Water | 55.23 | 55.31 | 54.41 |
| Pluronic F127 | 1 | 1 | 1 |
| PEG 8K | 5 | 5 | 5 |
| Lysine HCl | 4 | 4 | 4 |
| STPP | 2.5 | 2.5 | 2.0 |
| SAPP | 2.5 | 2.5 | 2.0 |

TABLE 9-continued

Exemplary Formulations

| Material | Composition A | Composition B | Composition C |
|---|---|---|---|
| Mirapol 8801 (41%) | 2.44 | 2.44 | 4.26 |
| Cetylpyridinium chloride | 0.075 | 0 | 0.075 |
| Preservative | 0.05 | 0.05 | 0.05 |
| Humectants | 27 | 27 | 27 |
| Flavors | 0.2015 | 0.2015 | 0.2015 |
| Colorant | 0.0006 | 0.0006 | 0.0006 |

TABLE 10

Commercial Formulation

| Material | Commercial Formulation |
|---|---|
| Water | q.s. |
| Pluronic F127 | 0.1-2 |
| PEG 8K | 0.0 |
| Lysine HCl | 0.0 |
| STPP | 0.0 |
| Mirapol 8801 (41%) | 0.0 |
| Cetylpyridinium chloride | 0.01-0.1 |
| Preservative | 0.01-0.1 |
| Humectants | 0-40 |
| Flavor | 0.05-1 |
| Color | 0.0001-0.005 |

The active attachment biofilm model (Extrecate et al., Caries Research 2010; 44:372-379) was used to measure antibacterial efficacy of biphasic mouthwash formulations. In this model, 24-HAP discs were clamped onto a sterile metal lid. The lid was then inoculated in 2% unstimulated saliva in McBain medium for 24 hours at 37°C on a 24-well plate under anaerobic conditions. After initial attachment, the biofilms were transferred into fresh growth media for maturation.

Treatment was performed after formation of biofilm (i.e., 24 hours). Discs were treated for 10 minutes at room temperature with 1.6 ml mouthwash formulations. The lid was subsequently transferred to a new plate for washing with 1.7 ml 25% Tryptic Soy Buffer (repeated 3 times). The biofilms were then transferred into McBain medium and incubated anaerobically at 37°C. The discs were treated seven times over a 5-day period and the resulting biofilms were harvested using sonication. The harvested biofilms were subjected to ATP metabolic assay (supplied by ThermoFisher Scientific) and plated on 5% sheep blood agar plate to determine total colony counts. Results were reported as log(CFU/ml) for four replicates of each samples.

TABLE 11

Antibacterial activity of tested formulations against Commercial Formulation

| Formulation | % Bacterial Reduction vs. Untreated |
|---|---|
| Composition A | 100% |
| Composition C | 95% |
| Commercial Formulation | 84% |

Table 11 above shows the biofilm percent reduction versus an untreated HAP disc. In comparison with the Commercial Formulation, both Compositions A and B performed at least as well within the margin of error of the experiment. Changes in polymer and polyphosphate levels did not show large effects.

Biofilms treated with either DV or polyphosphates may give a false indication of antibacterial efficacy when paired with CPC. These materials are known to prevent biofilm attachment (via anti-attachment mechanisms), which in turn may give the appearance of CPC efficacy. Further, when CPC is combined with DV and polyphosphates, the efficacy of CPC may be compromised through complexation, decreasing the bioavailability of the CPC. Thus, to test this effect, the analysis was repeated with compositions containing and omitting CPC (i.e., Compositions A and B), and compared to the Commercial Formulation, which is summarized below.

TABLE 12

Antibacterial activity of tested formulations against Commercial Formulation

| Formulation | % Bacterial Reduction vs. Untreated |
|---|---|
| Composition A | 96% |
| Composition B | 55% |
| Commercial Formulation | 97% |

In comparison to the Commercial Formulation, Composition B, which contained no CPC showed a 55% reduction of the biofilm vs. untreated. This result can be attributed to the combination of DV and polyphosphates contained within the formulation. However, When CPC is included in the composition (Composition A), the efficacy increases significantly, and was equivalent to the Commercial Formulation.

This data supports that biphasic compositions having a combination of DV and polyphosphates (i.e., STPP/SAPP) has excellent anti-bacterial efficacy comparable to commercial formulations. The data also shows that the tested compositions allow for the combination of CPC and DV/polyphosphate salts without compromise to antibacterial efficacy. This effect is achieved through the inclusion of Lys, which is shown to provide stability to a CPC-anionic material complex.

The efficacies of the tested compositions are further illustrated below in terms of the log of colony forming units (CFU), compared to a CPC-free formulation, Colgate Total, and an untreated sample.

TABLE 13

Antibacterial activity in terms of logCFU reduction of tested formulations against untreated

| Formulation | log CFU |
|---|---|
| Composition A | 7.6 |
| Composition B | 8.8 |
| Commercial Formulation | 7.6 |
| Untreated | 9.9 |

Example 7—Exemplary Formulations

Exemplary formulations were manufactured through the following method. A slurry of poloxamer and polyethylene glycol having a molecular weight of about 8,000 daltons is created. Once formed, polyphosphates (i.e., STPP and/or SAPP), lysine and Rhodia DV8801 were added. Next, cetyl pyridinium chloride is added, followed by all remaining formulation components. Generally, polyethylene glycol is added last to such formulations; however, it was found that adding the polyethylene glycol last resulted in a large increase in dissolving time, typically overnight.

Using the above method, the following compositions were created.

TABLE 14

Exemplary Formulations

| Material | Formulation 1 | Formulation 2 | Formulation 3 |
|---|---|---|---|
| Water | q.s. | q.s. | q.s. |
| Poloxamer | 1 | 1 | 1 |
| Lysine | 4 | 4 | 4 |
| Polyethylene Glycol (8,000D) | 5 | 5 | 5 |
| Rhodia DV8801 (in 41% solution) | 2.44 | 3.66 | 1.22 |
| Cetyl Pyridinium Chloride | 0.075 | 0.075 | 0.075 |
| Sodium Benzoate | 0.05 | 0.05 | 0.05 |
| Glycerin | 10 | 10 | 10 |
| Sorbitol | 10 | 10 | 10 |
| Propylene Glycol | 7 | 7 | 7 |
| Sodium Tripolyphosphate (STPP) | 2.5 | 2 | 2.5 |
| Sodium Acid Pyrophosphate (SAPP) | 2.5 | 2 | 2.5 |
| Flavorants and Colorants | 0.2 | 0.2 | 0.2 |
| Separation (Top/Bottom) | 34/66 | 60/40 | 36/64 |
| Separation factor (%, 30 min) | 58 | 49 | 45 |
| Separation factor (%, 60 min) | 93 | 98 | 79 |
| Viscosity (cP) | 26.6 | 32.8 | 24.2 |

What is claimed is:

1. An oral care composition comprising an aqueous solution comprising
   a) an acidic polymer;
   b) a nonionic polymer;
   c) at least one polyphosphate present in an amount of 1-6% by weight;
   d) a polyamine compound, wherein the polyamine is lysine, in free or salt form;
   e) a cationic active agent provided by an orally acceptable salt selected from zinc salts, stannous salts, chlorhexidine digluconate, and cetyl pyridinium chloride;
   f) an orally acceptable carrier; and
   g) water;
   wherein the solution comprises two distinct aqueous phases having a different composition and density.

2. The oral care composition of claim 1, wherein the polyphosphate comprises sodium tripolyphosphate, tetrasodium pyrophosphate, sodium acid pyrophosphate, tetrapotassium pyrophosphate, sodium hexametaphosphate or combinations thereof.

3. The oral care composition of claim 1, wherein the polyphosphate comprises a combination of sodium tripolyphosphate in an amount of 0.1-4% by weight and sodium acid pyrophosphate in an amount of 0.1-4% by weight.

4. The oral care composition of claim 1, wherein the acidic polymer is selected from one or more of synthetic anionic linear or branched polycarboxylates, phosphate/acrylate co-polymers, linear or branched sulfates and combinations thereof.

5. The oral care composition of claim 1, wherein the acidic polymer is a co-polymerized product of a mixture of acrylic acid, methacrylic acid, and a mixture of compounds of Formula 1:

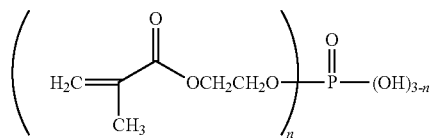

wherein n is 0, n is 1 and n is 2.

6. The oral care composition of claim 1, wherein the nonionic polymer is selected from polyethylene glycols, polypropylene glycols, poloxamers, and random polyethylene glycol/polypropylene glycol copolymers, and mixtures thereof.

7. The oral care composition of claim 1, wherein the composition comprises 40% to 65% water.

8. The oral care composition of claim 1, further comprising an anionic surfactant.

9. The oral care composition of claim 1 having a pH of 4.6-8.

10. The oral care composition of claim 1 having a viscosity of 10-40 cP.

11. The oral care composition of claim 1 which is oil-free, apart from flavoring agents.

12. The oral care composition of claim 1, wherein the composition is an oral care composition, wherein the ingredients are orally acceptable, and wherein the composition comprises one or more of a thickener, a buffer, a humectant, a surfactant, an abrasive, a sweetener, a flavorant, a pigment, a dye, an anti-caries agent, an anti-bacterial agent, a whitening agent, a desensitizing agent, a preservative, or a mixture thereof.

13. The oral care composition of claim 1, wherein the composition is a mouthwash.

14. The oral care composition of claim 1, wherein a first phase comprises:
   a) the nonionic polymer, and
   b) water; and
   a second phase comprises:
   a) the acidic polymer;
   b) at least one polyphosphate;
   c) the polyamine compound; and
   d) water,
   wherein the first phase is a top phase and the second phase is a bottom phase after separation.

15. The oral care composition of claim 1 wherein:
   a) the acidic polymer comprises a combination of a phosphate/acrylate co-polymer in a total amount of 1% to 5%;
   b) the nonionic polymer comprises a combination of (i) polyethylene glycol having an average molecular weight of 5 kDa to 35 kDa, and (ii) poloxamer 407, in a total amount of 0.1-2% polyethylene glycol and 0.5-1.5% poloxamer;
   c) the polyphosphate comprises sodium tripolyphosphate in an amount of 1-6%; or a combination of sodium tripolyphosphate and sodium acid pyrophosphate each present in an amount of about 0.1-4%;
   d) the polyamine, in free or salt form, is lysine;
   e) the water is present in an amount of 50-60%; and
   f) the cationic active agent is present in an effective amount, in free or orally acceptable salt form and comprises cetyl pyridinium chloride, in an amount of 0.05 to 0.1%,
   wherein the composition is a mouthwash, further comprising humectant, in an amount of 20-40%, and about 1%, flavoring, sweetener, preservative, and dye;
   wherein all ingredients are orally acceptable; and
   wherein all amounts are by weight of the total composition.

* * * * *

UNITED STATES PATENT AND TRADEMARK OFFICE
CERTIFICATE OF CORRECTION

PATENT NO. : 10,912,731 B2
APPLICATION NO. : 15/668913
DATED : February 9, 2021
INVENTOR(S) : Carl Myers et al.

Page 1 of 1

It is certified that error appears in the above-identified patent and that said Letters Patent is hereby corrected as shown below:

In the Claims

In Column 25, Line 49, in Claim 2, after "wherein the", insert -- at least one --.

In Column 25, Lines 52-53, in Claim 2, delete "or combinations thereof." and insert -- . --, therefor.

In Column 25, Line 54, in Claim 3, after "wherein the", insert -- at least one --.

In Column 25, Line 55, in Claim 3, delete "a combination of".

In Column 25 , Line 60, in Claim 4, before "linear", insert -- and --.

In Column 25, Lines 60-61, in Claim 4, delete "and combinations thereof." and insert -- . --, therefor.

In Column 25, Line 63, in Claim 5, after "product", delete "of" and insert -- comprising --, therefor.

In Column 26, Line 8, in Claim 5, delete "n is 1 and n is 2." and insert -- 1 or 2. --, therefor.

In Column 26, Line 15, in Claim 7, delete "composition comprises 40% to 65% water." and insert -- water comprises 40% to 65% by weight of the composition. --, therefor.

Signed and Sealed this
Twenty-fifth Day of May, 2021

Drew Hirshfeld
*Performing the Functions and Duties of the
Under Secretary of Commerce for Intellectual Property and
Director of the United States Patent and Trademark Office*